United States Patent
Terpstra

(10) Patent No.: US 7,572,959 B2
(45) Date of Patent: *Aug. 11, 2009

(54) PROCESS FOR CONTROLLING CYST NEMATODE POPULATION IN SOYBEANS

(75) Inventor: Mark A. Terpstra, Perry, IA (US)

(73) Assignee: Mark Seed Company, Perry, IA (US)

( * ) Notice: Subject to any disclaimer, the term of this patent is extended or adjusted under 35 U.S.C. 154(b) by 77 days.

This patent is subject to a terminal disclaimer.

(21) Appl. No.: 11/763,319

(22) Filed: Jun. 14, 2007

(65) Prior Publication Data

US 2007/0250944 A1 Oct. 25, 2007

Related U.S. Application Data

(63) Continuation of application No. 10/393,847, filed on Mar. 21, 2003, now Pat. No. 7,241,938, which is a continuation-in-part of application No. 09/207,350, filed on Dec. 8, 1998, now abandoned, and a continuation-in-part of application No. 09/689,809, filed on Oct. 13, 2000, now abandoned.

(60) Provisional application No. 60/075,299, filed on Feb. 20, 1998.

(51) Int. Cl.
*A01H 1/00* (2006.01)

(52) U.S. Cl. ........................ 800/312; 800/265; 800/260

(58) Field of Classification Search .................. None
See application file for complete search history.

(56) References Cited

U.S. PATENT DOCUMENTS

| | | | | |
|---|---|---|---|---|
| 5,648,318 | A | * | 7/1997 | Kraus et al. ................. 504/320 |
| 7,241,938 | B2 | * | 7/2007 | Terpstra ..................... 800/312 |

OTHER PUBLICATIONS

Hartwig, et al., 1982. Response of Resistant and susceptible Soybean Cultivars to Continuous Cropping in Area Infested with Cyst Nematode. Plant Disease. 66(1):pp. 18-20.

Young, et al., 1986. Response of Soybean Cyst Nematodes to Cropping Sequences. Plant Disease. 70(8):pp. 787-791.

Anand, et al. 1995. Effect of Temporal Deployment of Different Sources of Resistance to Soybean Cyst Nematode. J. Proc. Agric. 8(1): pp. 119-123.

Hartwig, et al. 1978. Registration of Bedford Soybeans. Crop Sci. 18:915.

Hartwig, et al. 1973. Registration of Forrest Soybeans. Crop Sci. 13:287.

* cited by examiner

*Primary Examiner*—Medina A Ibrahim
(74) *Attorney, Agent, or Firm*—Jondle & Associates, P.C.

(57) ABSTRACT

A method of controlling cyst nematode population in soybeans by providing a blended composition of soybean varieties. At least one of the soybean varieties in the blend has resistance to a given race spectrum, while another of the soybean varieties in the blend may have resistance to a differing race spectrum or be a susceptible variety. The blend may include 10 to 90% of the first variety and 90 to 10% of the second variety. The blend may consist of three or more soybean varieties.

8 Claims, No Drawings

PROCESS FOR CONTROLLING CYST NEMATODE POPULATION IN SOYBEANS

CROSS-REFERENCE TO RELATED APPLICATIONS

This application is a continuation of U.S. patent application Ser. No. 10/393,847 filed Mar. 21, 2003, now U.S. Pat. No. 7,241,938, which is a continuation-in-part of U.S. patent application Ser. No. 09/207,350 filed Dec. 8, 1998 now abandoned and U.S. patent application Ser. No. 09/689,809 filed Oct. 13, 2000, both now abandoned, both hereby incorporated by reference and which claim the benefit under Title 35 United States Code §119(e) of U.S. Provisional Application Ser. No. 60/075,299, filed Feb. 20, 1998 and hereby incorporated by reference.

STATEMENT REGARDING FEDERALLY SPONSORED RESEARCH OR DEVELOPMENT

Not Applicable.

AUTHORIZATION PURSUANT TO 37 C.F.R. §1.71 (D)(E)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to the field of soybean production, and more particularly to a method of controlling cyst nematode population in soybeans.

2. Description of the Related Art

Cyst nematodes are responsible for direct loss in soybean yield, and indirect losses due to cost of pesticides and non-optimal use of land or rotation. Soybean cyst nematodes (*Heterodera glycines*) have a negative economic impact that may exceed $500 million per year in the United States.

Economically significant densities of cyst nematodes usually cause stunting of crop plants. The root system is smaller than for uninfected plants, resulting in leaves showing symptoms of mineral deficiencies with an increased risk of wilting in dry soil conditions. Yield losses are related to the density of cyst nematode present at planting and in severe cases may be substantially above 50% for crops such as soybeans.

Current control methods include the use of chemicals, cultural techniques, and the use of resistant soybean varieties. Nematicides are considered to present significant health risks and cultural control such as crop rotation may be unacceptable to specialist growers or growers with few alternative crops.

Use of resistant soybean varieties does not provide adequate long-term control since cyst nematode race shift occurs. For example, if race 3 is present in a field and the farmer plants a race 3 resistant variety, within one year race shift occurs, i.e., race 3 mutates (race shifts) to race 1, 2, 4, etc. Therefore, the same race 3 resistant soybean variety is again susceptible to the new race spectrum of cyst nematode. Furthermore, cyst nematode is capable of race shifting at a rate faster than the industry can breed or engineer resistant varieties with high yields.

Those concerned with these and other problems recognize the need for an improved process for controlling cyst nematode population in soybeans.

BRIEF SUMMARY OF THE INVENTION

The present invention provides a method of controlling cyst nematode population in soybeans by providing a blended composition of soybean varieties. At least one of the soybean varieties in the blend has resistance to a given race, while another of the soybean varieties in the blend may be resistant to a race or be a susceptible variety. The blend may include 10 to 90% of the first variety and 90 to 10% of the second variety. The blend of the present invention may also include three or more soybean varieties. Planting the blended composition controls cyst nematode by forcing them into a dormant state, or by maintaining a specific race consistency that can be controlled in a field environment.

DETAILED DESCRIPTION OF THE INVENTION

The following Examples describe a process to control cyst nematode race shift and/or to force CN (cyst nematode) to become dormant by blending varieties of soybeans in the following combinations:

1. CN race resistant soybean variety+CN race resistant soybean variety;

2. CN race resistant soybean variety+CN race susceptible soybean variety;

3. CN race resistant genetically altered soybean variety+CN race resistant genetically altered soybean variety;

4. CN race resistant genetically altered soybean variety+CN race susceptible genetically altered soybean variety;

5. any other blend of soybean varieties for the express purpose of high yielding soybean varieties; and 6. combinations as explained below.

The following table provides an explanation of codes used in the examples and Tables 31 and 32.

TABLE 1

Explanation of codes:

| VARIETY | SOURCE OF SCN RESISTANCE: | RESISTANT TO: |
|---|---|---|
| A = | PI88788 | Race 3 & 4 |
| B = | PEKING | Race 1 & 3 |
| C = | PI437654 | Hartwig/Race 1, 2, 3, 4 & 5 |
| D = | PI209332 | Race resistant |
| E = | Susceptible | Unknown |
| F = | Unknown race resistant | Unknown source |
| G = | NSG | Race 3 & 14 |

DEFINITIONS

In the description and tables which follow, a number of terms are used. In order to provide a clear and consistent understanding of the specification and claims, including the scope to be given such terms, the following definitions are provided:

Resistant: As used herein, "resistant" or resistance means a soybean variety that is resistant to one or more races of Soybean Cyst Nematode (SCN). Where SCN attach to a resistant variety a majority of the nematodes die and/or do not reproduce.

Susceptible: As used herein, "susceptible" means a soybean variety susceptible to all races of Soybean Cyst Nematode. When SCN attach to a susceptible variety, the nematodes grow larger and reproduce.

Soybean Cyst Nematode (SCN): As used herein, "SCN" is a microscopic roundworm that attaches to soybean roots.

Cyst Nematode Race Spectrum: As used herein, "race spectrum" means a soybean variety having resistance to one or more races of SCN (i.e., spectrum of races).

Soybean Cyst Nematode Number (SCN #): As used herein, the "SCN #" is the number of SCN eggs per 100 cc of soil taken from the area adjacent to the soybean plant.

Transverse Blends: The reversal of a known or stated blend. Example: (90%) A×(10%) B if transgressed would be: (10%) A×(90%) B, or any other combination of stated varieties in any and all percentages between 10% and 90%.

CTA Soybean Blend: As used herein, a "CTA Soybean Blend" is a blend of seed of one or more SCN resistant soybean varieties with one or more susceptible soybean varieties.

CTB Soybean Blend: As used herein, a "CTB Soybean Blend" is a blend of seed of two or more SCN resistant soybean varieties.

Rotating: As used herein, "rotating" (rotation) means changing the soybean blend or crop planted from season to season on the same field. For example, a CTA soybean blend is planted in the first year, a CTB soybean blend is planted in the same field in the second year, corn (an alternate crop) is planted in the third year, a CTA blend is planted the fourth year, etc. Various soybean blends, individual SCN resistant and susceptible soybean varieties, and any alternate crop can be rotated from one growing season to the next in a given field.

EXAMPLES

The following examples are provided to further illustrate the present invention and are not intended to limit the invention beyond the limitations set forth in the appended claims.

Examples of resistant varieties of soybeans that could be used in lieu of the varieties identified in Table 1 are included as defined by brand name and maturity group in Table 32.

Examples of susceptible varieties of soybeans that could be used in lieu of the varieties identified in Table 1 are included as defined by brand name and maturity group in Table 33.

The present invention provides for a method of blending soybean varieties. In one preferred embodiment the blend consists of two or more varieties resistant to SCN (i.e., CTB). In another preferred embodiment the blend consists of one or two resistant varieties blended with a susceptible variety (i.e., CTA). The blend of the present invention may contain 10% to 90% of a first soybean variety and 90% to 10% of a second variety. In another preferred embodiment, two resistant varieties are blended with one susceptible variety where the blend contains 10% to 50% of a first resistant variety, 10% to 50% of a second resistant variety and 5% to 40% of a susceptible variety.

The blends produced by the method of the present invention result in 1) improved control and reduction of SCN number in the field and/or 2) improved yield compared versus the same varieties per se.

Example 1

Example Blends of Resistant and Susceptible Soybean Varieties

| | | |
|---|---|---|
| (90%) A × (10%) E | (90%) B × (10%) E | (90%) C × (10%) E |
| (80%) A × (20%) E | (80%) B × (20%) E | (80%) C × (20%) E |
| (70%) A × (30%) E | (70%) B × (30%) E | (70%) C × (30%) E |
| (60%) A × (40%) E | (60%) B × (40%) E | (60%) C × (40%) E |
| (90%) D × (10%) E | (90%) F × (10%) E | (90%) G × (10%) E |
| (80%) D × (20%) E | (80%) F × (20%) E | (80%) G × (20%) E |
| (70%) D × (30%) E | (70%) F × (30%) E | (70%) G × (40%) E |
| (60%) D × (40%) E | (60%) F × (40%) E | (60%) G × (40%) E |

*Any and all other blends.
*Any and all other blends of stated varieties in any and all combinations of percentages.

Example 2

Blends of Resistant and Resistant Soybean Varieties

| | | |
|---|---|---|
| **(90%) A × (10%) B | **(90%) B × (10%) A | **(90%) C × (10%) A |
| **(80%) A × (20%) C | **(80%) B × (20%) C | **(80%) C × (20%) B |
| **(70%) A × (30%) D | **(70%) B × (30%) D | **(70%) C × (30%) D |
| **(60%) A × (40%) F | **(60%) B × (40%) F | **(60%) C × (40%) F |
| **All Transverse blends | **All Transverse blends | **All Transverse blends |
| **(90%) A × (10%) A | **(90%) D × (10%) A | |
| **(80%) B × (20%) B | **(80%) D × (20%) B | |
| **(70%) C × (30%) C | **(70%) D × (30%) F | |
| **(60%) D × (40%) D | **(60%) D × (40%) C | |
| **(50%) E × (50%) E | **All Transverse blends | |
| **(40%) F × (60%) F | | |
| **All Transverse blends | | |
| **(90%) F × (10%) A | **(90%) G × (10%) A | |
| **(80%) F × (20%) B | **(80%) G × (20%) B | |
| **(70%) F × (30%) C | **(70%) G × (30%) C | |
| **(60%) F × (40%) D | **(60%) G × (40%) D | |
| **All Transverse blends | **(60%) G × (40%) F | |
| *Any and all other blends. | **All Transverse blends | |

*Any and all other blends of stated varieties in any and all combinations of percentages.
**Example of Transverse blend: (90%) A × (10%) B Transversed: (10%) A × (90%) B, or any other combination of stated varieties in any and all percentages.

Example 3

Blends of Resistant+Resistant×Susceptible Soybean Varieties

| | | |
|---|---|---|
| **(90%) (A + B) × (10%) E | **(90%) (B + C) × (10%) E | **(90%) (C + D) × (10%) E |
| **(80%) (A + C) × (20%) E | **(80%) (B + C) × (20%) E | **(80%) (C + F) × (20%) E |
| **(70%) (A + D) × (30%) E | **(70%) (B + F) × (30%) E | **(70%) (C + G) × (30%) E |

-continued

| | | |
|---|---|---|
| **(60%) (A + F) × (40%) E | **(60%) (B + G) × (40%) E | **(60%) (C + B) × (40%) E |
| *Any and all other blends | *Any and all other blends | *Any and all other blends |
| **All Transverse blends | **All Transverse blends | **All Transverse blends |
| **(90%) (D + F) × (10%) E | **(90%) (A + A) × (10%) E | |
| **(80%) (F + D) × (20%) E | **(80%) (B + B) × (20%) E | |
| **(70%) (D + C) × (30%) E | **(70%) (C + C) × (30%) E | |
| **(60%) (D + G) × (40%) E | **(60%) (D + D) × (40%) E | |
| *Any and all other blends | **(50%) (F + F) × (50%) E | |
| **All Transverse blends | **(40%) (G + G) × (60%) E | |
| | *Any and all other blends | |
| | **All Transverse blends | |

*Any and all other blends of stated varieties in any and all combinations of percentages.
**Example of transverse blend: (90%) A × (10%) B Transgressed: (10%) A × (90%) B, or any other combination of stated varieties in any and all percentages.

Example 4

Resistant & Susceptible Blend=A×E

| | | |
|---|---|---|
| Percentage: | 80% | 20% |
| Variety Type Example: | A | E |
| Stated Variety: | MRK 97CN33 | MRK 9829 |
| Appendix: | A | B |

Example 5

Resistant & Resistant Blend=A×A

| | | |
|---|---|---|
| Percentage: | 50% | 50% |
| Variety Type Example: | A | A |
| Stated Variety: | MRK 95CN27 | MRK 97CN33 |
| Appendix: | A | A |

Example 6

Resistant & Resistant & Susceptible Blend=(A+A)×E

| | | | |
|---|---|---|---|
| Percentage: | 40% | 40% | 20% |
| Variety Type Example: | A | A | E |
| Stated Variety: | MRK 95CN27 | MRK97CN33 | MRK 9829 |
| Appendix: | A | A | B |

Example 7

Resistant & Susceptible Blend=C×E

| | | |
|---|---|---|
| Percentage: | 60% | 40% |
| Variety Type Example: | C | E |
| Stated Variety: | Dwight | MRK 9826 |
| Appendix: | A | B |

Example 8

Resistant & Resistant Blend=G×A

| | | |
|---|---|---|
| Percentage: | 60% | 40% |
| Variety Type Example: | G | A |
| Stated Variety: | Hornback HBK58 | LG Seed JMS5009C |
| Appendix: | A | A |

Example 9

Resistant & Resistant & Susceptible Blend=(C+G)×E

| | | | |
|---|---|---|---|
| Percentage: | 30% | 40%) | 30% |
| Variety Type Example: | C | G | E |
| Variety: | Hartwick | Hornback HBK58 | MRK EX835 |
| Appendix: | A | A | B |

Example 10

The following Tables 2-9 summarize data from field trials conducted in the 1998 growing season on infested and non-infested plots. The variety or blend is listed in the first column. In the second column, SCN resistant (R) and susceptible (S) is identified for each variety and blend. Columns 3-6 are plant height, lodging score, bushels/acre and Kg/hectare respectively. Column 7 shows the initial (early season) SCN # eggs/ 100 cc soil. Column 8 shows the final (late season or after harvest) SCN # eggs per 100 cc soil. Column 9 shows the % change in SCN#.

TABLE 2

Kanawha INFESTED Variety Trial

| Entry | SCN | Height (in) | Lodging | Bu/acre | Kg/hectare | SCN# (initial) | SCN# (final) | Egg/100 c.c. soil % Chg |
|---|---|---|---|---|---|---|---|---|
| 98CN26 | R | 33.5 | 1.0 | 41.5 | 2434 | 7775 | 2875 | −271 |
| 97CN29 | R | 32.8 | 1.6 | 46.7 | 2737 | 3750 | 1967 | −191 |
| 98CN26-7 98CN26CTB | 50% R 50% R | 35.0 | 1.0 | 42.2 | 2473 | 6100 | 1475 | −414 |
| Mean GroupII Resistant | R | 32.7 | 1.8 | 40.1 | 2352 | 5564 | 2498 | |
| Mean GroupII Susceptible | S | 30.9 | 1.7 | 34.5 | 2023 | 6450 | 5825 | |

As shown in Tables 2 and 3, a blend of two (2) resistant varieties were compared to each of the two (2) resistant varieties, 98CN26 and 97CN29, which were not blended. In Table 2 unexpectedly there was a greater reduction in SCN number with the blend of two resistant varieties.

| Varieties Tested: | |
|---|---|
| 98CN26 | resistant variety - not a blend |
| 97CN29 | resistant variety - not a blend |
| 98CN26-7 | resistant variety × resistant variety: 98CN26 (60%) × 97CN29 (40%) |

As shown in Table 4, unexpectedly the 40% susceptible and 60% resistant blended variety 9829 CTA had equal or higher yield compared to the two resistant varieties or the susceptible variety and had a lower SCN number than resistant variety 98CN30.

TABLE 3

Kanawha NONINFESTED Variety Trial

| Entry | SCN | Height (in) | Lodging | Bu/acre | Kg/hectare | SCN# (initial) | Egg/100 c.c.soil SCN# (final) |
|---|---|---|---|---|---|---|---|
| 98CN26 | R | 40.3 | 1.0 | 46.1 | 2700 | NA | NA |
| 97CN29 | R | 38.0 | 1.5 | 53.2 | 3115 | NA | NA |
| 98CN26-7 98CN26CTB | 50% R 50% R | 44.0 | 1.5 | 52.1 | 3051 | NA | NA |
| Mean GroupII Resistant | R | 37.9 | 1.8 | 53.2 | 3116 | NA | NA |
| Mean GroupII Susceptible | S | 36.8 | 1.9 | 53.8 | 3153 | NA | NA |

TABLE 4

Ames INFESTED Variety Trial

| Entry | SCN | Height (in) | Lodging | Bu/acre | Kg/hectare | SCN# (initial) | SCN# (final) | Egg/100 c.c. soil % Change |
|---|---|---|---|---|---|---|---|---|
| 9829 | S | 30.8 | 1.0 | 52.4 | 3068 | 1575 | 5138 | +327 |
| 98CN30 9829CTA | 40% S 60% R | 41.0 | 1.6 | 54.2 | 3175 | 1725 | 2800 | +163 |
| 98CN30 | R | 40.0 | 1.5 | 46.4 | 2718 | 3937 | 9675 | +246 |
| Mean GroupII Resistant | R | 36.1 | 2.0 | 55.5 | 3250 | 2484 | 1733 | |
| Mean GroupII Susceptible | S | 35.8 | 2.1 | 49.6 | 2907 | 2231 | 4563 | |
| Mean GroupIII Resistant | R | 43.5 | 2.1 | 53.4 | 3126 | 2467 | 2150 | |
| Mean GroupIII Susceptible | S | 39.1 | 1.8 | 49.3 | 2891 | 1400 | 6194 | |

TABLE 5

Ames NONINFESTED Variety Trial

| Entry | SCN | Height (in) | Lodging | Bu/acre | Kg/hectare | Egg/100 c.c. soil SCN# (initial) | SCN# (final) |
|---|---|---|---|---|---|---|---|
| 9829 | S | 39.3 | 1.3 | 64.8 | 3794 | NA | NA |
| 98CN30-9 9829CTA | 40% S 60% R | 46.5 | 1.5 | 60.7 | 3556 | NA | NA |
| 98CN30 | R | 48.3 | 2.3 | 60.9 | 3569 | NA | NA |
| Mean GroupII Resistant | R | 43.3 | 2.5 | 61.4 | 3596 | NA | NA |
| Mean GroupII Susceptible | S | 41.4 | 2.5 | 61.2 | 3586 | NA | NA |
| Mean GroupIII Resistant | R | 49.3 | 2.5 | 58.3 | 3419 | NA | NA |
| Mean GroupIII Susceptible | S | 44.7 | 2.0 | 58.6 | 3432 | NA | NA |

TABLE 6

Crawfordsville INFESTED Variety Trial

| Entry | SCN | Height (in) | Lodging | Bu/acre | Kg/hectare | Egg/100 c.c. soil SCN# (initial) | SCN# (final) |
|---|---|---|---|---|---|---|---|
| 9829 | S | 19.8 | 1.1 | 23.6 | 1379 | 5825 | NA |
| 97CN33-9 | R | 25.5 | 1.0 | 29.8 | 1747 | 7600 | NA |
| 98CN30 | R | 20.0 | 1.0 | 18.9 | 1103 | 3550 | NA |
| 97CN33 | R | 25.0 | 1.0 | 30.5 | 1785 | 4625 | NA |
| Mean GroupII Resistant | R | 22.4 | 1.1 | 25.6 | 1501 | 5960 | NA |
| Mean GroupIII Resistant | R | 26.1 | 1.1 | 32.9 | 1925 | 5377 | NA |
| Mean GroupIII Susceptible | S | 20.9 | 1.0 | 20.5 | 1203 | 4833 | NA |

TABLE 7

Crawfordsville NONINFESTED Variety Trial

| Entry | SCN | Height (in) | Lodging | Bu/acre | Kg/hectare | Egg/100 c.c. soil SCN# (initial) | SCN# (final) |
|---|---|---|---|---|---|---|---|
| 9829 | S | 26.3 | 1.4 | 44.8 | 2627 | NA | NA |
| 97CN33-9 | R | 37 | 1.4 | 48.5 | 2843 | NA | NA |
| 98CN30 | R | 34.3 | 1.4 | 49.2 | 2881 | NA | NA |
| 97CN33 | R | 32.8 | 1.3 | 43.4 | 2543 | NA | NA |
| Mean GroupII Resistant | R | 33.5 | 1.7 | 47.1 | 2762 | NA | NA |
| Mean GroupIII Resistant | R | 36.2 | 1.5 | 47.9 | 2806 | NA | NA |
| Mean GroupIII Susceptible | S | 34.5 | 1.6 | 45.3 | 2651 | NA | NA |

As shown in Table 8, for each of the SCN resistant varieties not blended, there was a decrease in the final count of the SCN infestation. The 98CN26 showed a decrease of 270%, and 97CN29 had 190% decrease. Unexpectedly, in the blended variety, the final count decreased 413% which was significantly greater than in either of the un-blended varieties. This indicates a greater ability to control the SCN infestation through blending.

Ames Infested Variety Trial

| Varieties Tested: | |
|---|---|
| 9829 | susceptible variety - not a blend |
| 98CN30 | resistant variety - not a blend |
| 98CN30-9 | resistant variety × susceptible variety: 98CN30 (60%) × 9829 (40%) |

TABLE 8

Kanawha INFESTED Variety Test

| Entry | SCN | Ht (in) | Loding | Bu/Acre | Kg/ Hectare | SCN# (initial) | SCN# (final) | Egg/100 c.c. soil Increase (%) | Egg/100 c.c. soil Decrease (%) |
|---|---|---|---|---|---|---|---|---|---|
| 98CN26 | R | 33.5 | 1 | 41.5 | 2434 | 7775 | 2875 | | 270.43% |
| 97CN29 | R | 32.8 | 1.6 | 46.7 | 2737 | 3750 | 1967 | | 190.65% |
| 98CN26-7 98CN26CTB | R + R | 35 | 1 | 42.2 | 2473 | 6100 | 1475 | | 413.56% |

As shown in Table 9, a blend of one (1) resistant variety 98CN30 and one (1) susceptible variety 9829 is compared versus each of the blend components separately.

As expected, the susceptible variety demonstrated a dramatic increase (326%) in the final SCN count, while the resistant variety showed moderate increase (245%). Unexpectedly, the final SCN count in the blended bean, 98CN30-9 (9829CTA), showed a significantly lower SCN number increase of 162%. Therefore, showing an overall lower infestation and the ability to control populations.

In addition, the blended soybean, 98CN30-9 unexpectedly showed the most desirable traits of increasing or maintaining yield, while having the least increase of Cyst Nematode populations.

Both Tables 8 and 9 variety trials show the blended soybeans have an enhanced ability to control cyst nematode population.

The method of the present invention is believed to work on cyst nematode by either forcing them into a dormant state, or by blending the soybeans together in a way that enables the farmer to maintain a specific race that can then be controlled in a field environment, such as a blend of race resistant and race susceptible.

The purpose of blending resistant varieties of one (1) race with a resistant variety of another race, or resistant varieties of one (1) race with a susceptible variety may allow the farmer to eliminate cyst nematode and/or place them in a dormant state, and/or maintain race consistency of a controllable type within the field.

One major advantage of this technique is that it is no longer necessary to plant continuous corn, or to continually change soybean varieties as the CN mutates, or race shifts. Additionally, this technology controls the SCN rather than try to keep up with the race shifts as in the past.

Example 11

In another embodiment of the present invention, CTA (Cyst Tech® Level A), CTB (Cyst Tech® Level B) and alternate crops such as corn and alfalfa are rotated in subsequent growing seasons for a given field. CTA is a blend of both resistant and susceptible soybean varieties. CTB is a blend of resistant varieties for one or more SCN races. Unexpectedly, rotation of CTA and CTB has resulted in improved yields and/or reduced counts of soybean cyst nematode (SCN). This unexpected result indicates cyst populations are controlled

TABLE 9

Ames INFESTED Variety Test

| Entry | SCN | Height (in) | Lodging | Bu/Acre | Kg/ Hectare | SCN# (initial) | SCN# (final) | Egg/100 c.c. soil Increase (%) | Egg/100 c.c. soil Decrease (%) |
|---|---|---|---|---|---|---|---|---|---|
| 9829 | S | 30.8 | 1.0 | 52.4 | 3068 | 1575 | 5138 | 326.22% | |
| 98CN30-9 9829CTA | R + S | 41.0 | 1.6 | 54.2 | 3175 | 1725 | 2800 | 162.32% | |
| 98CN30 | R | 40.0 | 1.5 | 46.4 | 2718 | 3937 | 9675 | 245.75% | | more effectively when using the method of the present invention versus planting conventional cyst resistant soybeans for two or more generations. When planting conventional resistant soybean varieties the soybean cyst nematode race shifts to a new resistant race. In the method of the present invention Cyst Tech® Level A (CTA) controls the cyst race in one or more growing seasons, and then by rotating with Cyst Tech® Level B (CTB) in a succeeding growing season, this gives an unexpected result of a reduced SCN population (SCN count) for all races of SCN.

In another embodiment of the present invention, CTA is rotated with CTB in alternate years (or growing seasons). For example, Cyst Tech® Level A (CTA) is planted the first year, while Cyst Tech® Level B (CTB) is planted on the same land the following year. This rotation can be repeated over a number of growing seasons. In another example, CTA is grown for two or more consecutive seasons followed by growing CTB for one or more seasons. Alternatively, corn or another alternate crop can periodically be rotated with soybeans as shown in Table 10, columns 3-8. The rotation of CTA, CTB and an alternate crop can be used in any combination; including the examples shown in Table 10. The determination of whether CTA, CTB or an alternate crop is grown in the next growing season is based on current year data on soybean yield, plant health and appearance, SCN counts versus previous years data and the use of specific SCN resistant varieties in previous years. In one preferred embodiment, a lower SCN count, predominantly a SCN Race 3 environment is obtained to produce higher soybean yields.

TABLE 10

Examples of Rotation Patterns

| Year | 2 | 3 | 4 | 5 | 6 | 7 | 8 |
|---|---|---|---|---|---|---|---|
| 1 | CTA | CTB | CTA | CTB | CTA | CTB | Corn |
| 2 | CTB | Corn | CTA | Corn | CTB | Corn | CTA |
| 3 | CTA | CTB | Corn | CTA | CTB | Corn | CTA |
| 4 | CTB | Corn | CTA | Corn | Corn | CTA | CTA |
| 5 | CTA | CTA | CTB | CTA | CTB | CTA | CTA |
| 6 | CTB | Corn | Clover | CTA | CTA | CTB | Corn |
| 7 | CTA | CTB | CTA | CTB | CTA | Clover | CTA |

The method of the present invention includes all possible rotation patterns for growing CTA and CTB and all rotation patterns for growing CTA and CTB with an alternative crop. The alternative crops are primarily non-host crops to SCN, including: corn, forages, sorghum, oats, rye, canola, sunflowers, cotton, rice and any other crop species.

In a preferred embodiment of the present invention, a CTB variety is grown for one season, followed by at least one season of growing a CTA variety. The CTB variety reduces the SCN count, as shown in Example 13, while the CTA variety maintains a lower SCN count versus a resistant line per se as shown in Example 12. Rotating the CTB variety, followed by the CTA variety, results in a predominantly SCN Race 3 environment. A predominantly SCN Race 3 environment generally aids in the expression of high soybean yields.

Example 12

As shown in Table 11, soybean variety MRK9829CTA is compared versus two commercial varieties. MRK9829CTA is a blend of MRK9829 and MRK98CN30. Unexpectedly, the CTA variety, (which is a blend of 60% resistant MRK98CN30 and 40% susceptible soybean variety MRK9829) had a higher yield and a smaller increase in Final SCN count versus the resistant and the susceptible varieties per se. CTA varieties have shown 3 distinct advantages versus commercial varieties. 1) CTA varieties reduce SCN race shift over one or more seasons; 2) CTA varieties had improved control over cyst populations and 3) CTA varieties maintain a higher yield versus conventional commercial varieties in the presence of cyst-infected fields.

The SCN initial count is taken prior to or early in the growing season and the SCN final count is taken late in the growing season or after harvest.

TABLE 11

| Variety | SCN | Plant Height | Ldg | Bushels/ Acre | KG per Hectare | SCN # (Initial Count) | SCN # (Final Count) | SCN # Increase (%) |
|---|---|---|---|---|---|---|---|---|
| MRK9829 | S | 30.8 | 1.0 | 52.4 | 3068 | 1575 | 5138 | 326.22% |
| MRK9829CTA | 40% S 60% R | 41.0 | 1.6 | 54.2 | 3175 | 1725 | 2800 | 162.32% |
| MRK98CN30 | R | 40.0 | 1.5 | 46.4 | 3937 | 3937 | 9675 | 245.75% |

Based on the results in Table 11, this environment is a non-race 3 environment, where varieties resistant to SCN race 3 have been previously grown.

Example 13

As shown in Table 12, soybean blend MRK98CN26CTB is compared to SCN resistant varieties MRK97CN29 and MRK98CN26. MR98CN26CTB (CTB) is a blend of 40% MRK97CN29 and 60% MRK98CN26. Unexpectedly the CTB variety had a 414% decrease in SCN count when compared to the other two resistant varieties. CTB varieties show two distinct advantages, including: 1) CTB varieties had improved control over the SCN population; and 2) CTB varieties maintain high yields consistent with non-cyst infected fields as shown in Table 2. As shown in Table 12, CTB varieties reduced cyst count significantly versus the other individual varieties per se.

The SCN initial count is taken prior to or early in the growing season and the SCN final count is taken late in the growing season or after harvest.

Based on the results in Table 12, this environment is a predominantly race 3 environment, where varieties susceptible to Race 3 SCN were previously grown.

TABLE 12

| Variety | SCN | Plant Height | Ldg | Bushels/Acre | KG per Hectare | SCN # (Initial Count) | SCN # (Final Count) | % Change |
|---|---|---|---|---|---|---|---|---|
| MRK97CN29 | R | 32.8 | 1.6 | 46.7 | 2737 | 3750 | 1967 | 190.65% |
| MRK98CN26 | R | 33.5 | 1.0 | 41.5 | 2434 | 7775 | 2875 | 270.43% |
| MRK98CN26CTB | 50% R 50% S | 35.0 | 1.0 | 42.2 | 2473 | 6100 | 1475 | 413.56% |

For example, in another embodiment of the present invention, by rotating MRK9829CTA with MRK98CN26CTB over two or more growing seasons, this results in a higher yielding soybean environment and/or a decrease in the final SCN count.

In Tables 13 through 30, columns 1-3 show the first variety, % of variety, and if the variety is SCN resistant or susceptible. If the percent in column 2 equals 100%, then this is not a blend but the variety listed in column 1 per se. Columns 4, 5 and 6 show the second variety name, if a blend, the percent of the variety 2 in the blend and the SCN resistance or susceptibility respectively. Columns 7 and 8 show the SCN #1 value which is the first SCN count taken earlier in the growing season, the second SCN count (SCN #2) which is the SCN count taken later in the season. Column 9 shows the percent change in SCN count from SCN #1 to SCN #2 and equals SCN #2 divided by SCN #1. Column 10 shows the yield of the variety in bushels per acre.

2002 Data Perry, IA

TABLE 13

| Variety 1 | % | SCN | Blend Variety 2 | % | SCN | SCN #1 | SCN #2 | % Change | Bu/A |
|---|---|---|---|---|---|---|---|---|---|
| RR0221 | 100 | S | | | | 5200 | 15840 | +205 | 44.45 |
| RR0221CTA-1 | 40 | S | RR022SCN | 60 | R | 13260 | 5160 | −257 | 46.08 |
| RR0022 | 100 | R | | | | | | | |

TABLE 14

| Variety 1 | % | SCN | Blend Variety 2 | % | SCN | SCN #1 | SCN #2 | % Change | Bu/A |
|---|---|---|---|---|---|---|---|---|---|
| RR0023 | 100 | S | | | | 7020 | 7860 | 12 | 48 |
| RR0023CTA-1 | 40 | S | RR0022SCN | 60 | R | 5120 | 4280 | −120 | 6249 |
| RR0022SCN | 100 | R | | | | | | | |

TABLE 15

| Variety 1 | % | SCN | Blend Variety 2 | % | SCN | SCN #1 | SCN #2 | % Change | Bu/A |
|---|---|---|---|---|---|---|---|---|---|
| RR0125 | 100 | R | | | | 9780 | 3480 | −281 | 50.1 |
| RR0125CTB-1 | 60 | R | RR0026SCN | 40 | R | 7080 | 1640 | −432 | 62.29 |
| RR0125CTB-2 | 60 | R | RR9923SCN | 40 | R | 6420 | 320 | −2006 | 64.03 |
| RR0125CTB-4 | 60 | R | RREX26SCN | 40 | R | 7500 | 120 | −6250 | 61.57 |
| RR0125CTB-5 | 60 | R | RR0125SCN | 40 | R | 12240 | 360 | −3400 | 51 |

TABLE 16

| Variety 1 | % | SCN | Blend Variety 2 | % | SCN | SCN #1 | SCN #2 | % Change | Bu/A |
|---|---|---|---|---|---|---|---|---|---|
| RR0225 | 100 | | | | | 6960 | 6240 | −10 | 47.24 |
| RR0225CTA | 40 | S | RR0125SCN | 60 | R | 2960 | 800 | −370 | 52.94 |
| RR0125 | 100 | R | | | | 9780 | 3480 | −281 | 50.1 |

TABLE 17

| Variety 1 | % | SCN | Blend Variety 2 | % | SCN | SCN #1 | SCN #2 | % Change | Bu/A |
|---|---|---|---|---|---|---|---|---|---|
| RR0025 | 100 | S | | | | 7440 | 12960 | 74 | 41.99 |
| RR0025CTA-1 | 40 | S | RREX0126SCN | 60 | R | 4000 | 2320 | −172 | 41.38 |
| RR0025CTA-2 | 40 | S | RREX0126SCN | 60 | R | 7620 | 4560 | −167 | 63.91 |
| RR0025CTA-3 | 40 | S | RREX26SCN | 60 | R | 8220 | 1040 | −790 | 56.84 |
| RR025CTA-4 | 40 | S | RR0125SCN | 60 | R | 6000 | 4040 | −149 | 56.21 |
| RR025SCN | 100 | R | | | | 9780 | 3480 | −281 | 50.1 |

TABLE 18

| Variety 1 | % | SCN | Blend Variety 2 | % | SCN | SCN #1 | SCN #2 | % Change | Bu/A |
|---|---|---|---|---|---|---|---|---|---|
| RR0126 | 100 | S | | | | 7200 | 7080 | 2 | 59.02 |
| RR0126CTA | 40 | S | RR0125SCN | 60 | R | 6420 | 1360 | −472 | 65.84 |
| RR0126CTA-1 | 40 | S | RREX0125SCN | 60 | R | 12480 | 2640 | −473 | 52.35 |
| RR0126CTA-2 | 40 | S | RR0026SCN | 60 | R | 5520 | 4080 | −135 | 54.77 |
| RR0126CTA-4 | 40 | S | RR0229SCN | 60 | R | 8160 | 1600 | −510 | 80.23 |
| RR0126CTA-5 | 40 | S | RR9927SCN | 60 | R | 7500 | 4120 | −182 | 55.95 |
| RR0125 | 100 | R | | | | 9780 | 3480 | −281 | 50.1 |

TABLE 19

| Variety 1 | % | SCN | Blend Variety 2 | % | SCN | SCN #1 | SCN #2 | % Change | Bu/A |
|---|---|---|---|---|---|---|---|---|---|
| RR0226 | 100 | S | | | | 2880 | 4680 | 63 | 51.71 |
| RR0226CTA-3 | 40 | S | RR0026SCN | 60 | R | 4920 | 5760 | 17 | 63.91 |

TABLE 20

| Variety 1 | % | SCN | Blend Variety 2 | % | SCN | SCN #1 | SCN #2 | % Change | Bu/A |
|---|---|---|---|---|---|---|---|---|---|
| RR26 | 100 | S | | | | 6240 | 13320 | +214 | 44.64 |
| RR26CTA | 40 | S | RREX0126SCN | 60 | R | 12480 | 9600 | −130 | 49.26 |
| RR26CTA-1 | 40 | S | RR0026SCN | 60 | R | 3840 | 1600 | −240 | 51.36 |
| RR26CTA-2 | 40 | S | RREX26SCN | 60 | R | 4200 | 2080 | −202 | 40.06 |
| RR26GTA-4 | 40 | S | RR9927SCN | 60 | R | 5880 | 3120 | −188 | 58.61 |
| RR26GTA-3 | 40 | S | RR0229SCN | 60 | R | 3720 | 3560 | −104 | 5392 |
| RR26GTA-6 | 40 | S | RR0029SCN | 60 | R | 7200 | 2600 | −277 | 69.03 |

TABLE 21

| Variety 1 | % | SCN | Blend Variety 2 | % | SCN | SCN #1 | SCN #2 | % Change | Bu/A |
|---|---|---|---|---|---|---|---|---|---|
| RR9927 | 100 | S | | | | 3660 | 3780 | 3 | 52.00 |
| RR9927CTA | 40 | S | RR0229SCN | 60 | R | 4920 | 3540 | −139 | 58.00 |
| RR9927CTA-1 | 40 | S | RR9927SCN | 60 | R | 8520 | 680 | −1253 | 61.25 |
| RR9927CTA-2 | 40 | S | RR0028SCN | 60 | R | 8400 | 2160 | −389 | 51.69 |
| RR9927CTA-3 | 40 | S | RR0128SCN | 60 | R | 8760 | 9480 | 8 | 58.65 |
| RR9927CTA-5 | 40 | S | RR0126SCN | 60 | R | 9120 | 1200 | −760 | 58.43 |

TABLE 22

| Variety 1 | % | SCN | Blend Variety 2 | % | SCN | SCN #1 | SCN #2 | % Change | Bu/A |
|---|---|---|---|---|---|---|---|---|---|
| RR0029CTB | 50 | R | RR0028SCN | 50 | R | 14980 | 1800 | −832 | 55.38 |
| RR0029CTB-1s | 50 | R | RR0029SCN | 50 | R | 3480 | 1600 | −218 | 65.08 |
| RR0029CTB-2 | 50 | R | RR0129SCN | 50 | R | 6540 | 920 | −711 | 66.27 |
| RR0029CTB-3 | 50 | R | RR0128SCN | 50 | R | 9480 | 1560 | −608 | 59.94 |

TABLE 23

| Variety 1 | % | SCN | Blend Variety 2 | % | SCN | SCN #1 | SCN #2 | % Change | Bu/A |
|---|---|---|---|---|---|---|---|---|---|
| RR0129CTB | 60 | R | RR0028SCN | 40 | R | 3800 | 1560 | −244 | 63.05 |
| RR0129CTB-1 | 60 | R | RR0128SCN | 40 | R | 10800 | 950 | −1137 | 65.6 |
| RR0129CTB-2 | 60 | R | RR0029SCN | 40 | R | 3880 | 880 | −441 | 59.73 |
| RR0129CTB-3s | 60 | R | RR0129SCN | 40 | R | 18960 | 4120 | −460 | 54.35 |
| RR0129CTB-4 | 60 | R | RREX32ASCN | 40 | R | 7800 | 1440 | −542 | 61.25 |

TABLE 24

| Variety 1 | % | SCN | Blend Variety 2 | % | SCN | SCN #1 | SCN #2 | % Change | Bu/A |
|---|---|---|---|---|---|---|---|---|---|
| RR0231 | 100 | S | | | | 3720 | 6600 | 77 | 47.12 |
| RR0231CTA-1 | 40 | S | RREX32SCN | 60 | R | 4200 | 1920 | −219 | 56.77 |
| RR0231CTA-2 | 40 | S | RR0033SCN | 60 | R | 3080 | 2040 | −151 | 68.52 |
| RR0231CTA-3 | 40 | S | RR0133SCN | 60 | R | 8040 | 3240 | −248 | 47.19 |
| RR0231CTA-4 | 40 | S | RR9933SCN | 60 | R | 2840 | 3300 | 16 | 60.55 |

TABLE 25

| Variety 1 | % | SCN | Blend Variety 2 | % | SCN | SCN #1 | SCN #2 | % Change | Bu/A |
|---|---|---|---|---|---|---|---|---|---|
| RREX32ACTB | 60 | R | RR0029SCN | 40 | R | 5160 | 3300 | −156 | 62.35 |
| RREX32ACTB-1 | 60 | R | RR0129SCN | 40 | R | 7620 | 2200 | −346 | 63.86 |
| RREX32ACTB-2 | 60 | R | RR0033SCN | 40 | R | 6480 | 1380 | −470 | 64.6 |
| RREX32ACTB-3 | 60 | R | RR0133SCN | 40 | R | 24960 | 12840 | −194 | 52.96 |
| RREX32ACTB-4 | 60 | R | RR9933SCN | 40 | R | 12000 | 13080 | 9 | 59.77 |
| RREX32ACTB-5s | 60 | R | RREX32ASCN | 40 | R | 4680 | 4800 | 3 | 60.76 |

TABLE 26

| Variety 1 | % | SCN | Blend Variety 2 | % | SCN | SCN #1 | SCN #2 | % Change | Bu/A |
|---|---|---|---|---|---|---|---|---|---|
| RR0133CTB | 60 | R | RR0029SCN | 40 | R | 8400 | 1520 | −553 | 48.72 |
| RR0133CTB-1 | 60 | R | RR0129SCN | 40 | R | 3792 | 1400 | −271 | 42.26 |
| RR0133CTB-2 | 60 | R | RR0033SCN | 40 | R | 4200 | 2680 | −157 | 60.62 |
| RR0133CTB-3s | 60 | R | RR0133SCN | 40 | R | 3280 | 2000 | −164 | 43.68 |

TABLE 27

| Variety 1 | % | SCN | Blend Variety 2 | % | SCN | SCN #1 | SCN #2 | % Change | Bu/A |
|---|---|---|---|---|---|---|---|---|---|
| RR9933CTB | 60 | R | RR0029SCN | 40 | R | 4740 | 3360 | −141 | 63.89 |
| RR9933CTB-1 | 60 | R | RR0129SCN | 40 | R | 4620 | 440 | −105 | 56.1 |
| RR9933CTB-2 | 60 | R | RR0033SCN | 40 | R | 27120 | 7440 | −365 | 62.59 |
| RR9933CTB-3s | 60 | R | RR9933SCN | 40 | R | 27360 | 3180 | −860 | 59.18 |
| RR9933CTB-4 | 60 | R | RR0133SCN | 40 | R | 15600 | 3300 | −473 | 57.45 |

TABLE 28

| Variety 1 | % | SCN | Blend Variety 2 | % | SCN | SCN #1 | SCN #2 | % Change | Bu/A |
|---|---|---|---|---|---|---|---|---|---|
| RR0033CTB | 60 | R | RR0029SCN | 40 | R | 3960 | 2160 | −1356 | 57.17 |
| RR0033CTB-1 | 60 | R | RR0129SCN | 40 | R | 2360 | 2040 | −116 | 59.71 |
| RR0033CTB-2s | 60 | R | RR0033SCN | 40 | R | 3540 | 1600 | −347 | 60.97 |
| RR0033CTB-3 | 60 | R | RR0133SCN | 40 | R | 15120 | 7200 | −581 | 49.04 |
| RR0033CTB-4 | 60 | R | RREX35SCN | 40 | R | 4200 | 1480 | −413 | 59.64 |

TABLE 29

| Variety 1 | % | SCN | Blend Variety 2 | % | SCN | SCN #1 | SCN #2 | % Change | Bu/A |
|---|---|---|---|---|---|---|---|---|---|
| RR9934 | 100 | S | | | | 960 | 2600 | 59 | 46.87 |
| RR9934CTA-1 | 40 | S | RR0033SCN | 60 | R | 1800 | 1080 | −167 | 53.65 |
| RR9934CTA-2 | 40 | S | RR0133SCN | 60 | R | 3720 | 3060 | −122 | 50.9 |
| RR9934CTA-4 | 40 | S | RREX35SCN | 60 | R | 30480 | 6350 | −479 | 47.96 |

TABLE 30

| Variety 1 | % | SCN | Blend Variety 2 & 3 | % | SCN | SCN #1 | SCN #2 | % Change | Bu/A |
|---|---|---|---|---|---|---|---|---|---|
| RREX3CTA | 20 | S | RR0029 | 40 | R | 35760 | 9600 | −373 | 55.86 |
| | | | RR0028 | 40 | R | | | | |
| RREX3CTA BSM | 20 | S | RREX32A | 40 | R | 11280 | 6360 | −177 | 59.09 |
| | | | RR9933 | 40 | R | | | | |
| RREX#CTB BSM | 20 | S | RREX32A | 40 | R | 3960 | 3760 | −105 | 58.2 |
| | | | RR9933 | 40 | R | | | | |

Example 14

An example of the rotation method of the present invention is shown in Table 31.

TABLE 31

| Year | Variety | Eggs/100 cc soil | Bu/Acre |
|---|---|---|---|
| 1998 | Susceptible | 20,000 | 30 |
| 1999 | 9527CTB | 5,000 | 50 |
| 2000 | Corn | | |
| 2001 | 9927CTA | 2,000 | 52 |

In 1998 a resistant variety was grown in a field in Onawa, Iowa. As shown in Table 31, the SCN# in the field was measured at 20,000 and the variety yielded 30 bu/acre. In 1999 a CTB variety 9527CTB was planted in this same field in Onawa, Iowa. Unexpectedly, in the fall of 1999, the SCN# dropped to 5,000 and also the bushels per acre increased to 50 bu/acre. Corn was grown on this land the following year in 2000. In 2001, a CTA variety 9927CTA was grown, which unexpectedly reduced the SCN# to 2,000 and increased the yield to 52 bushels/acre. In this field, the method of the present invention had resulted in both an increased yield and a reduction in the SCN number.

Examples of SCN resistant soybean varieties are shown in Table 32. Examples of SCN susceptible soybean varieties are shown in Table 33. "NSG" indicates that the seed company did not provide the source for the SCN resistance. "RR" indicates that this variety is a "Roundup Ready" variety in addition to being SCN resistant.

(Roundup Ready is a registered trademark of Monsanto Chemical Company).

TABLE 32

| Brand/Variety | Source of SCN Resistance |
|---|---|
| RESISTANT VARIETIES MATURITY GROUP I | |
| Great Lakes GL 1559 | P188788 |
| Hy-Vigor Jazz | P188788 |
| Latham 352 CN | P188788 |
| Novartis (NK) | P188788 |
| Pioneer 9182 | P188788 |

TABLE 32-continued

| Brand/Variety | Source of SCN Resistance |
|---|---|
| Prairie PB 156 CN | P188788 |
| Prairie PB 188 CN | P188788 |
| ProfiSeed PS 197 N | P188788 |
| (Public, IL) Bell | P188788 |
| (Public, MN) Freeborn | P188788 |
| (Public, MN) Faribault | P1209332 |
| Stine 1882 | P188788 |
| RESISTANT VARIETIES MATURITY GROUP II | |
| AgriPro AP 2601 SCN | P188788 |
| AgriPro AP 2901 SCN | P188788 |
| AgVenture AV-1294 | NSG |
| Asgrow A2540 | P188788 |
| Asgrow A2869 | P188788 |
| Asgrow AG2901 (RR) | P188788 & Peking |
| Callahan 4277 | NSG |
| Callahan 6299 | NSG |
| Coop 199N | NSG |
| Dairyland DSR 296 N | P188788 |
| DeKalb CX 235 C | P188788 |
| DeKalb CX 260 C | P188788 |
| DeKalb CX 292 C | P188788 |
| Diener Bros DB 926 C | P188788 |
| Diener Bros DB 272 C | P188788 |
| Diener Bros DB 280 C | P188788 |
| Diener Bros DB 2900 CR (RR) | NSG |
| Garst D267N | P188788 |
| Golden Harvest H-1286 | P188788 |
| Great Lakes GL 2533 N | P188788 |
| Great Lakes GL 2912 N | P188788 |
| Griffith PL 2885 | NSG |
| Growmark FS HS 2711 | P188788 |
| Growmark FS HS 2951 | P188788 |
| Gutwein 7282 C | NSG |
| Gutwein 7284 C | NSG |
| Henkel SS NBC | MSG |
| Hy-Vigor Braxton | P188788 |
| Kaltenberg KB 258 N | P188788 |
| Kruger K 2220 SCN | P188788 |
| Latham 522 CN | P188788 |
| Latham 722 CN | P188788 |
| LG Seeds LG 6296C | P188788 |
| Mark MRK97 CN-22 | P188788 |
| Mark MRK95 CN-27 | P188788 |
| Merschman Osage III SCN | P188788 |
| Merschman Cherokee VIII | P188788 |
| Midwest G-2162 N | P188788 |
| Midwest G-2520 N | P188788 |
| 221 C | P188788 |

TABLE 32-continued

| Brand/Variety | Source of SCN Resistance |
|---|---|
| MWS 262 C | P188788 |
| MWS 270 CN | P188788 |
| MWS 291 CN | P188788 |
| Mycogen 5291 | P188788 |
| NC + 2N18 | P188788 |
| NC + 2N87 | P188788 |
| Novartis (NK) S29-11 | P188788 |
| Patriot 210 N | P188788 |
| Patriot 262 N | P188788 |
| Pioneer 9234 | Peking |
| Pioneer 92B91 | P188788 |
| Prairie PB 215 CN | P188788 |
| Prairie PB 221 CN | P188788 |
| Prairie PB 299 CN | P188788 |
| Profiseed PS 227 N | P188788 |
| Profiseed Z 465 N | P188788 |
| Profiseed PS 2465 N | Peking |
| (Public, IL) Jack | P188788 |
| (Public, IL) Dwight | P188788 |
| (Public, IA) IA 2036 | P188788 |
| Roeschley 8246 C | NSG |
| Sieben SS 282 N | P188788 |
| Stine 2472 | P188788 |
| Stine 2972 | P188788 |
| Sun Ag SAS 2812 | NSG |
| Sunstar 2994 CN | P188788 |
| Tri County Stockdale GA 2797 | P188788 |
| Trilser Trisoy 2812 | NSG |
| UAP Seed DG 3227 N | P188788 |
| UAP Seed DG 3281 N | P188788 |
| Wilken 2441 N | P188788 |
| Wilken 2571 CN | P188788 |
| Wilken 2681 | P188788 |
| Wilson 2100 SCN | P188788 |
| RESISTANT VARIETIES MATURITY GROUP III | |
| Adler 305 | NSG |
| AgraTech AT 333 | P188788 |
| AgraTech AT 345 | P188788 |
| AgraTech AT 350 | P188788 |
| AgraTech AT 39 RR | P188788 |
| AgriPro Ap 3601 SCN | P188788 |
| AgVenture AV 1335 | NSG |
| AgVenture AV 1351 | NSG |
| Asgrow A 3134 | P188788 |
| Asgrow AG 3301 RR | P188788 & Peking |
| Asgrow A 3431 | P188788 & Peking |
| Asgrow A 3559 | P188788 |
| Asgrow AG 3701 RR | P188788 & Peking |
| Asgrow A 3732 | P188788 |
| Asgrow A 3904 STS | P188788 & Peking |
| Baird Seed B-3292 | NSG |
| Beck 334 | P188788 |
| Beck 3440 RR | P188788 |
| Beck 382 CN | P188788 |
| Berg.-Taylor BT 386 C | P188788 |
| Berg.-Taylor BT 398 CR (RR) | P188788 |
| Berg.-Taylor BT 399 C | P188788 |
| Brown Arise 336-C | NSG |
| Brown Arise 375-C | NSG |
| Brown Arise 378 C | NSG |
| Brown Arise 398 C | NSG |
| Midland 8394 N (RR) | NSG |
| Midland 8395 N (RR) | NSG |
| Callahan 7331 | Peking |
| Callahan 337 N | P188788 |
| Callahan 7388 | P188788 |
| Campbell 327 N | NSG |
| Campbell 383 N | NSG |
| Crows 33004 | P188788 |
| Dairyland DSR 325 | P188788 |
| Dairyland DSR 373 | P188788 |
| Dairyland DSR 371 RR | P188788 |
| DeKalb CX 339 C | P188788 |
| DeKalb CX 340 C | P188788 |
| DeKalb CX 394 C | P188788 |
| Diener Bros DB 329 C | P188788 |
| Diener Bros DB 359 C | P188788 |
| Diener Bros XB 936 STS | P188788 |
| Diener Bros DB 369 | P188788 |
| Diener Bros DB 3850 CR (RR) | P188788 |
| Fontanelle F 3376 | NSG |
| Garst D 358 | P188788 |
| Gateway 373 | P188788 |
| Golden Harvest H-1337 | P188788 |
| Golden Harvest-H 1365 | P188788 |
| Golden Harvest X-390 RR | P188788 |
| Good Buddy GB 30 C | P188788 |
| Great Heart G-395 C | P188788 |
| Great Heart GT-398 C RR | NSG |
| Great Lakes GL 3434 | P188788 |
| Griffith PL 3305 | NSG |
| Growmark HS RT 316 (RR) | P188788 |
| Growmark 327 N | P188788 |
| Growmark HS 3361 | P188788 |
| Growmark HS 3471 | P188788 |
| Growmark 359 N | P188788 |
| Growmark HS 3411 | P188788 |
| Growmark 377 N | P188788 |
| Growmark HS 3961 | P188788 |
| Growmark HS 3971 | P188788 |
| Growmark FS HS 3971 | P188788 |
| Gutwein 7323 C | NSG |
| Gutwein 7350 C | NSG |
| Gutwein 7393 C | NSG |
| Hoblit HB333 | P188788 |
| Hubner 337 N | NSG |
| Hubner 351 N | NSG |
| Hubner 357 N | NSG |
| HyVigor 333 | P188788 |
| IMC V346 | NSG |
| IMC V373 | NSG |
| IMC V395 | NSG |
| Kitchen KSC 329 C | NSG |
| Kitchen KSC 332 C | NSG |
| Kruger K 3444 SCN | P188788 |
| Lewis 334 | NSG |
| Lewis 3500 STS | NSG |
| Lewis 367 C | NSG |
| Lewis 362 | NSG |
| Lewis 388 | NSG |
| Lewis 3800 | NSG |
| Lewis 391 | NSG |
| Lewis 3901 | NSG |
| LG Seeds LG 6343 C | P188788 |
| LG Seeds LG 6355 C RR | P188788 |
| LG Seeds LG 6384 C | P188788 |
| LG Seeds LG 6399 C RR | P188788 |
| Mark MRK97 CN-33 | P188788 |
| Merschman McKinly II | P188788 & Peking |
| MFA Morsoy 538 | P188788 |
| Midwest G-3600 N | P188788 |
| Midwest G-3720 N | P188788 |
| Midwest G-3922 N RR | P188788 |
| Midwest X-96400N | P188788 |
| Moweaqua MS 336 | NSG |
| Moweaqua MS 361 | NSG |
| Moweaqua MS 376 | NSG |
| Moweaqua MD 8395 (RR) | NSG |
| Munson 335-3 | NSG |
| MWS 301 CN | P188788 |
| MWS 323 C | P188788 |
| MWS 340CN | P188788 |
| MWS 362C | P188788 |
| Mycogen 5331 | P188788 |
| Mycogen 5376 | P188788 |
| NC + 3N55 RR | P188788 |
| NC + 3A96 | P188788 |
| Novartis (Ciba) 3376 | P188788 |
| Novartis (NK) S 39-11 | P188788 |
| Patriot 311 N | NSG |
| Patriot 331 N | P188788 |
| Patriot 332 N | P188788 |
| Patriot 356 N | NSG |

TABLE 32-continued

| Brand/Variety | Source of SCN Resistance |
|---|---|
| Patriot 372 N | P188788 |
| Patriot 379 N | P188788 |
| Patriot 383 N | P188788 |
| Pioneer 93B11 | P188788 |
| Pioneer 9362 | P188788 |
| Pioneer 9363 (RR) | P188788 |
| Pioneer 93B83 | P188788 |
| Prairie PB 303 CN | P188788 |
| Prairie PB 383 CN | P188788 |
| (Public, IL) Cartter | P188788 |
| (Public, IL) Pana | P188788 |
| (Public, IL) Saline | P188788 |
| (Public, IL) Fayette | P188788 |
| (Public, IL) Maverick | P188788 |
| (Public, IL) Linford | P188788 |
| (Public, IL) Yale | P188788 |
| (Public, MO) Maverick | P188788 |
| (Public, MO) Saline | P188788 |
| (Public, IA) IA 3005 | P188788 |
| Quality Q 355C | NSG |
| Reeds Brand 355 SCN | P188788 |
| Roeschley 8372C | NSG |
| Schneider S336C | NSG |
| Schneider S366C | NSG |
| Schneider S379C | NSG |
| Schultz 3315 N | NSG |
| Schultz 3815 N | NSG |
| Excel 9391 N RR | NSG |
| Scott's Columbo II | NSG |
| Scott's Concorde | NSG |
| Scott's Cyster STS | NSG |
| Scott's Excel 8391 N RR | NSG |
| Stewart SB 3099 | P188788 |
| Stewart SB 3799 | P188788 |
| Stewart SB 3899 | P188788 |
| Stine 3272 | P188788 |
| Stone SE-3301 | NSG |
| Sun Ag SAS 3172 | NSG |
| Sunstar 3230 CN | P188788 |
| Sunstar 3590 CN | P188788 |
| Terra TS 325 | Peking |
| Terra TR 390 SCN | NSG |
| Trisler Trisoy 3210 | NSG |
| Trisler Trisoy 3342 | NSG |
| Trisler Trisoy 3716 | NSG |
| Trisler Trisoy 3744 | NSG |
| Trisler Trisoy 3867 RR | NSG |
| UAP Seed DG 3331 N | P188788 |
| UAP Seed DG 3378 N | P188788 |
| VanHorn VH 335 N | NSG |
| VanHorn VH 376 N | NSG |
| VanHorn VH 387 N | NSG |
| Wildy WS EX 32087 | NSG |
| Wildy WS 3508 | NSG |
| Wildy WS EX 37036 | NSG |
| Wilken 3431 CN | P188788 |
| Wilson 3330 SCN | P188788 |
| RESISTANT VARIETIES MATURITY GROUP IV | |
| Agra Tech AT 425 | P188788 |
| Agra Tech AT 460 | P188788 |
| AgriPro AP 4001 SCN | P188788 |
| AgriPro HY 4540 SCN | P188788 |
| AgriPro HY 458 SCN | P188788 |
| AgVenture AV 1445 | NSG |
| Asgrow A 4138 | P188788 |
| Asgrow AG 4401 RR | P188788 & Peking |
| Asgrow AG 4501 RR & STS | P188788 & Peking |
| Asgrow 4601 RR | P188788 & Peking |
| Asgrow 4604 STS | P188788 |
| Asgrow AG 4701 RR | P188788 & Peking |
| Asgrow AG 4702 RR | P188788 & Peking |
| Asgrow A 4715 | P188788 & Peking |
| Asgrow AG 4901 RR | P188788 & Peking |
| Asgrow A 4922 | P188788 |
| Beck 454 | P188788 |
| Beck 460 RR | P188788 |
| Berg.-Taylor BT 408 CR (RR) | P188788 |
| Berg.-Taylor BT 428 C | P188788 |
| Berg.-Taylor BT 436 C | P188788 |
| Berg.-Taylor BT 468 CR (RR) | P188788 |
| Berg.-Taylor BT 445 C | P188788 |
| Brown Arise 418 C | NSG |
| Brown Arise 427 C | NSG |
| Brown Arise 435 C | NSG |
| Midland 8471 N (RR) | NSG |
| Brown Arise 498 C | NSG |
| Callahan 6435 | P188788 |
| Callahan 6440 | P188788 |
| Callahan 7467 | P188788 |
| Crows 45002 | P188788 |
| DeKalb CX 420 C | P188788 |
| DeKalb CX 450 C | P188788 |
| DeKalb CX 469 C | P188788 |
| DeKalb CX 470 C | P188788 |
| DeKalb CX 499 C | P188788 |
| Diener Bros DB 404 C | P188788 |
| Deiner Bros DB 442 C | P188788 & Peking |
| Deiner Bros DB 4650 CR (RR) | P188788 |
| Deiner Bros DB 4620 CR (RR) | P188788 |
| Deiner Bros DB 472 C | P188788 |
| Gateway 425 | P188788 |
| Gateway 441 | P188788 |
| Gateway 451 | P188788 |
| Gateway 481 | P188788 |
| Gateway 493 | Peking |
| Golden Harvest H-1432 | P188788 |
| Golden Harvest H-1454 | P188788 |
| Golden Harvest H-1487 | P188788 |
| Good Buddy GB 402 C | P188788 |
| Great Heart G-424-C | P188788 |
| Great Heart G-465 C | P188788 |
| Great Lakes GL 4548 | P188788 |
| Growmark HS 4161 | P188788 |
| Growmark HS 4110 | P188788 |
| Growmark HS 4161 | P188788 |
| Growmark HS 4426 | P188788 |
| Growmark RT 446 (RR) | P188788 |
| Growmark HS 4801 | Peking |
| Gutwein 7439 C | NSG |
| Hartz H 4994 | P188788 |
| Hartz H 4994 (RR) | P188788 |
| Hartz H 4998 (RR) | P188788 |
| Hornbeck HBK 4600 | NSG |
| Hornbeck HBK 4755 | NSG |
| Hornbeck SB HBK R4898 (RR) | NSG |
| Hornbeck HBK 49 | NSG |
| IMC V443 | NSG |
| IMC V455 | NSG |
| Kitchen KSC 402 C | NSG |
| Lewis 405 | NSG |
| Lewis 431 | NSG |
| LG Seeds LG 6437 C | P188788 |
| LG Seeds LG 6462 C | P188788 |
| Merschman Richmond IV | P188788 |
| Merschman Houston IV | NSG |
| Merschman Memphis IV | P188788 |
| MFA Morsoy 4067 SCN | P188788 |
| MFA Morsoy 444 SCN | P188788 |
| Midwest G-4014 N | P188788 |
| Midwest G-4320 N | P188788 |
| Mycogen 429 | P188788 |
| NC + 4A27 | P188788 |
| NC + 4N78 RR | P188788 |
| Novartis (NK) S 46-44 | P188788 |
| Novartis S 46-W8 | P188788 |
| Patriot 412 N | P188788 |
| Patriot 420 N | P188788 |
| Patriot 442 N | P188788 |
| Patriot 452 N | Peking & P188788 |
| Patriot 457 N | P188788 |
| Patriot 482 N | P188788 |
| Pioneer 94B01 (RR) | P188788 |
| Pioneer 94B41 (RR) | P188788 |

TABLE 32-continued

| Brand/Variety | Source of SCN Resistance |
|---|---|
| Pioneer 9451 | P188788 |
| Pioneer 9481 | P188788 |
| Pioneer 9492 (RR) | P188788 |
| (Public, IN) Bronson | P188788 |
| (Public, SIU) Nile | Peking |
| (Public, SIU) Pyramid | Peking & P188788 |
| (Public, SIU) Pharaoh | Peking |
| (Public, SIU) Egyptian | Peking |
| (Public, MO) Delsoy 4210 | P188788 |
| (Public, MO) Mustang | P188788 |
| (Public, MO) Delsoy 4500 | Peking |
| (Public, MO) Avery | Peking & P188788 |
| (Public, MO) Delsoy 4710 | P1209332 & Peking |
| (Public, MO) Delsoy 4900 | Peking |
| (Public, TN) TN 4-86 | P188788 |
| (Public, TN) TN 4-94 | P188788 & Peking |
| Reeds Brand 350 SCN | Peking & P188788 |
| Schultz 4215 N | NSG |
| Schultz 4515 N | NSG |
| NE 4758 N RR | NSG |
| SS Coop FFR 414 | P188788 |
| SS Coop RT 446 (RR) | NSG |
| SS Coop FFR-478 | P188788 |
| Stewart SB 4490 | P188788 |
| Stewart SB 4640 | P188788 & Peking |
| Stewart SB 466R (RR) | P188788 |
| Stine 4322 | P188788 |
| Stine 4562 | P188788 |
| Stone SE-4397 N | NSG |
| Terra TS 4292 | P188788 |
| Terra TS 466 RR | NSG |
| Terra TS 4792 | P188788 |
| Terral TV 4479 | P188788 |
| Terral TV 4770 | P188788 |
| Trisler Trisoy 4064 | NSG |
| Trisler Trisoy 4212 | NSG |
| Trisler Trisoy 4432 | NSG |
| VanHorn VH 4340 N | NSG |
| Wildy WS EX 52 | NSG |
| Wildy WS 4305 | NSG |
| Wildy WS 4505 | NSG |
| Wildy WS 4845 | NSG |
| RESISTANT VARIETIES MATURITY GROUP V | |
| AgVenture AV 1504 | NSG |
| Asgrow A5403 | Peking & P188788 |
| Asgrow A5545 | NSG |
| Asgrow A5547 | P188788 & Peking |
| Asgrow A 5704 | P188788 & Peking |
| Asgrow A5801 RR | P188788 & Peking |
| Asgrow A5843 | P188788 & Peking |
| Asgrow A5848 | P188788 & Peking |
| Asgrow AG5951 RR | P188788 & Peking |
| Asgrow A 5959 | P188788 & Peking |
| Callahan 5510 | P188788 |
| DeKalb CX 510 C | P188788 |
| DeKalb CX 570 C | NSG |
| Delta Pine DP 3519 S | P188788 |
| Delta Pine DP 5352 | P188788 & Peking |
| Delta Pine DP 5644 RR | P188788 & Peking |
| Delta Pine DP 3588 | Peking & P188788 |
| Delta Pine 5806 RR | P188788 & Peking |
| Delta Pine DP 5960 RR | P188788 & Peking |
| Delta Pine DP 3571 S | P188788 |
| Delta Pine DP 415 | Peking |
| Gateway 511 | Peking |
| Golden Harvest H-1500 | P188788 |
| Great Lakes GL5123 | P188788 |
| Growmark HS 5199 | P188788 |
| Growmark HT 551 STS | P188788 |
| Gutwein 7525 C | NSG |
| Gutwein 7530 C | NSG |
| Hartz H 5218 | Peking |
| Hartz H 5545 | Peking |
| Hartz H 5545 (RR) | Peking |
| Hartz H 5350 | P188788 |
| Hartz 5350 (RR) | P188788 |
| Hartz H 5164 (RR) | P188788 |
| Hartz H 5566 (RR) | P188788 |
| Hartz H 5088 | Peking |
| Hartz H 5088 (RR) | Peking |
| Hartz H 5488 | Peking |
| Hornbeck HBK 5149 | NSG |
| Hornbeck SB HBK R5411 (RR) | NSG |
| Hornbeck SB HBK R5588 | NSG |
| Hornbeck HBK 54 | NSG |
| Hornbeck HBK 5770 | NSG |
| Hornbeck HBK 58 | NSG |
| LG Seeds JMS 5009C | Peking |
| MFA Morsoy 9152 SCN | P188788 |
| NC + 5A15 | P188788 |
| NC + 5A44 | P188788 |
| NC + 5A45RR (RR) | P188788 |
| Novartis (Ciba) 3505 | Peking |
| Novartis (NK) S57-11 | P188788 & Peking |
| Novartis (NK) S59-V6 (RR) | P188788 |
| Novartis (NK) S59-60 | P188788 & Peking |
| Patriot 537 N | P188788 |
| Patriot 555 N | P188788 |
| Pioneer 9521 | Peking |
| Pioneer 9552 | P188788 |
| Pioneer 9584 | Peking |
| Pioneer 9593 | Peking |
| (Public, KS) KS 5292 | Peking |
| (Public, MO) Hartwig | P1437654 & Peking |
| (Public, MO) Delsoy 5500 | Peking & P188788 |
| (Public, MO) Rhodes | P188788 |
| (Public, MS) Bedford | Peking & P188788 |
| (Public, MS) Forrest | Peking |
| (Public, TN) TN 5-95 | P188788 & Peking |
| Schultz 5015 N | NSG |
| SS Coop RT 540 (RR) | NSG |
| SS Coop FFR-542 | NSG |
| SS Coop FFR-595 | P188788 |
| Terra TS 504 | Peking |
| Terral TV 5495 | Peking |
| Terral TV 5797 | Peking |
| Terral TV 5893 | P188788 |
| Terral TV 5926 | P188788 |
| Trisler Trisoy 5170 | NSG |
| RESISTANT VARIETIES MATURITY GROUP VI | |
| Asgrow AG6101 RR | P188788 & Peking |
| Asgrow A6297 | P188788 & Peking |
| Asgrow A6711 | P188788 & Peking |
| Asgrow A6961 | P188788 & Peking |
| Delta Pine DP 3640 | P188788 |
| Delta Pine DP 3681 | Peking |
| Hartz H 6104 | Peking |
| Hartz H 6200 | Peking |
| Hartz H 6686 (RR) | NSG |
| Hornbeck HBK 6600 | P188788 |
| Hornbeck HBK 67 | NSG |
| Novartis (NK) S60-E4 (RR) | P188788 & Peking |
| Novartis (NK) S62-62 | P188788 |
| Novartis (NK) S65-50 | P188788 & Peking |
| Novartis (NK) S67-70 | P188788 & Peking |
| Pioneer 9692 | Peking |
| (Public, TN) TN 6-90 | Peking |
| Terral TV 6253 | Peking |
| Terral TV 6792 | Peking |
| Terral TV 6696 | P188788 |

TABLE 32-continued

| Brand/Variety | Source of SCN Resistance |
|---|---|
| RESISTANT VARIETIES MATURITY GROUP VII | |
| Delta Pine DP 3733 | P188788 |
| Hartz H 7440 | P188788 |
| Hartz H 7550 (RR) | Peking |
| Hornbeck HBK 79 | NSG |
| Novartis (NK) S73-Z5 (RR) | Peking & P188788 |
| Novartis (NK) S75-55 | P188788 & Peking |
| Pioneer 9711 | Peking |
| Pioneer 9761 | Peking |
| Pioneer 97B61 | P188788 |
| RESISTANT VARIETIES MATURITY GROUP VIII | |
| Novartis (NK) S83-30 | Peking |
| Novartis C 6738 | Peking |

Examples of SCN susceptible varieties are shown in Table 33.

TABLE 33

AgriPro Seeds Inc., Ames, IA (515-232-0891)
AP1953, AP1995, AP2220, AP25985, AP2995, AP3250, AP3414, AP3616, AP3868, AP2880
Albert Lee Seed Housn, Albert Lee, MN (507-373-3181)
1796, 2397
Callahan Seeds, Westfield, IN 9317-896-5551)
6330, 7221x, 7250x, 7317, 7383, 8200x, 8275, 8363
Cenex/Laud O'Lakes, Fort Dodge, IA (515-576-7311)
L2126, L2646, L2779
Crow's Hybrid Corn Co., Milford, IL (615-889-4151)
19001, 20001, EX0222, 25005, 28003, 32003, 33003, EX0426, EX0536, 38004, 30007
Custom Farm Seed, Momence, IL (815-472-2433)
CFS215, CFS290
Dairyland Seed Company, Inc., West Bend, WI (800-236-0163)
DSR-173, DSR-180/STS, DSA-195, DSA-220/STS, DSR-220/STS, DSR-246/STS, DSA-271/RR, DSR-277, DSR-293/RR, DSA-300, DSR-325, DSR-314/STS
Dale Ewing Seed, Jewell, IA (515-827-5114)
165, 170, 199, 202, 230RX, 241R, 244, 250, 255, 260+, 265, 270
DeKalb Genetics Corporation, DeKalb, IL (815-756-7333)
CX197, CX205, CX212, CX228, CX229, CX232, CX252, CX267, CX278, CX289, CX313, CX314, CX351, CX368, CX377, CX399
Dennis Ewing Farm Seed, Ames, IA (515-732-6236)
1991, 2162, 2221, 2221*, 2404, 2535, 2625, 2729, 2727*, 2727B, 2777, 2808*, 2818*, 2088, 3000, 3132, 3132*, 3230, 3424A, 3454, 3505B, 3550B, 3777, 3919, 4040*, D34Exp, D18Exp
Domestic Seed & Supply, Inc., Madison, SD (605-256-6529)
M 1190, M 2200, M 2259, M 2270
Farm Aventage, Clarion, IA (515-825-3682)
FA 1924, FA 2065, FA 2177, FA 2477, FA 2486, FA 2532, FA 2743
Fontanelle Hybrids, Nickerson, NE (402-721-1410)
2232, 3303, 3373
Four Star Seed Co., Parkersburg, IA (319-346-2162)
4266, 4267, 4270A, 4334, 4450K
Garst Seed Company, Slater, IA (515-585-3574)
Ex7173, D180, EX7265, EX7224, 0260, 0308, D331, EX7346, EX7357
GMA Seed Co., Old Lyme, CT (860-434-7999)
SV13020
Gold Country Seed, Inc., Norwood, MN (612-467-4320)
Odin, X3719, X3721, X5622,
Golden Seed Co., Cordova, IL (800-421-1156)
JC Robindson Seed Co., Waterloo, NE (800-228-9906)
H1184, H1190, H1194, H1211, H1218, H1237, H1236, H1269, H1279, H1295, H1315, H1353, X214, X282
Great Lakes Hybrids, Ovid, MI (617-834-2251)
GL1872, GL2334, GL2415, GL, 2772, GL2818, GL3101
Growmark Inc., Bloomington, IL (309-557-6399)
HS2171, 215, HT221, HS2561, HS2861, HS3071, 3251, HS3362
Hills Seed Co. Ellsworth, IA (515-836-2141)
EX238, EX248, EX268, EX278, HS1960, HS2170, HS2270, HS2570, HS259, HS2860, HS2970, HS3260, HS3360
Hoegemeyer Hybrids, Hooper, NE (402-654-3399)
191, 202, 225, 253, 312, 365, 380
Hy-Vigor Sands, Pauline, IA (712-448-2187)
2025, EX: 203, 2350, 2375, 2400, 3990
Illinois Ag. Exp. Stn., Urbana, IL
Bell, Caisay79, Iroquois, Jack, Macon, WilliamsBZ
Indiana Ag. Exp. Stn., West Layfette, IN
Probst
Iowa Ag. Exp. Stn., Ames, IA
Archer, HP204, IA1005, IA1006, IA1007, IA2007R, IA2008R, IA2011, IA2012, IA2013, IA2016, IA2017, IA2018, IA2019, IA2020, IA2021, IA2022, IA2034, IA2035, IA2036, IA2037, IA3001, IA3002, IA3004, IA3005, IA3006, IA3008, IA3009, Kenwood94, LS301, Marcus95, Pella86, VintonB1
Jacobsen Hybrid Corn Co. Inc., Lakeview, IA (712-657-2841)

TABLE 33-continued

J659, J679, J750, J756, J772, J774, J777, J844, J859, J865, J876, J956, J960, J971
Kaltenberg Seed Farms, Waunakee, WI (800-383-3276)
KB208, KB214, KB225, KB245, KB259, KB366
Caup Seed Co., West Point, NE (402-372-5588)
23344, 2451, KS1977, KS2474, KS2685, KS2774, KS2865, KS2887, KS2977, KS3287, KS3464
Kruger Seed Co., Dike, IA (800-772-2721)
K-1777, K-1990, K-1990*, K-2021*, K-2025, K-2343*, K-2425, K-2425, K-2525, K-2535*, K-2625*, K-2625, K-2725, K-2727*, K-2828, K-3032*, K-S032, K-3040, K-3222, K-3232*, K-3424, K-3505, K-3525E, K-3525, K-3535*, K-3737, K-3777, K-3939*, ˆ21 RR Ex,
ˆ242Roundup, ˆ25 RR Ex, ˆ28 RR Ex, ˆ36 RR Ex, ˆ36+ RR Ex
KSC/Challenger Sd Company, Cedar Falls, IA (319-989-2256)
K-2545
Latham Seed Co., Alexander, IA (515-692-3258)
250 Brand, 392 Brand, 410 Brand, 590 Brand, 621 Brand, 660 Brand, 662 Brand, 680 Brand, 720 Brand, 841 Brand, 950 Brand, 962 Brand, 1140 Brand, EX-324STS, EX-330, EX-420, EX-640, EX-710, EX-730
Lewis Hybrids Inc., Ursa, IL (217-964-2131)
310, 322, 360, 363, 390
LG Seeds, Mount Pleasant, IA (319-385-2299)
LG6212, LG6236STS, LG6245, LG6288, LG6339, LG6369
Maple Leaf Foods Intl., Toronto, Ontario (416-480-6420)
WJ130563
Mark Seed Co., Perry, IA (800-383-6275)
EX823, EX824, EX921, MRK9519, MRK9533, MRK9632, MRK9721, MRK9721-4, MRK9721-9, MRK9727-S, MRK9732, MRK9733, MRK97CN33, MRK9825, MRK9825-5, MRK9826, MRK9826-0, MRK9826-7, MRK9827, MRK9827-5, MRK9827-7, MRK9828, MRK9829, MRK9833, MRK9926, MRKEX835, MRKEX9333
Mels Seed & Feed, Lemars, IA (712-548-4131)
GM2810, GM2640
Mellow Dent Seed, Alla, IA (712-296-3663)
Coop Seed, Alla, IA (712-756-3663)
1289, 6191, 6221, 6231, 0244, 6251, 6252, 6292, 5333, 5334, 6335, 6361
Merschman Seeds, Westpoint, IA (319-837-8711)
MarsIV, ApacheV, CheyenneV, MoheganII, MohaveIII, ChickasawIII, HarrisonIV, TrumanV, FillmoreIV, EisenhowerIV, MadisonV,
Midland Soybean Development Assoc., Garden City, MO (816-852-8203)
94, 92, 9435, 9536, 9733*, RR2351
Midwest Seed Genetics Inc., Carroll, IA (800-369-8215)
G-1885, G-1912, G-1930, G-2112, G-2440, G-2454, G-2519, G-2818, G-2910, G-3141, G-3242, G-3300, G-3410, G-3626, G-3996
Minnesota Ag. Exp. Stn., St. Paul, MN
Parker, Sturdy
Mitchell Seeds, Buckingham, IA (319-478-8598)
2596
Mycogen Seeds, St. Paul, MN (800-Mycogen)
200, 5205, 5251, 5318, 5337, 5348
Naylor Seed Co., Scotch Grove, IA (800-747-7333)
NS1980, NS2150, NS2170, NS2250, NS2270, NS2380, NS2470, NS2670, NS2685STS, NS2750, NS2755STS, NS2770, NS3380, NS3470
NC+ Hybrids, Lincoln, NE (402-467-2517)
1A88, 2A15, 2A22, 2A42, 2A70, 2A99, 3A26, 3A44, 3A67
Nebraska Ag. Exp. Stn., Lincoln, NE
NE2596, NE3396, NE3297, Nemaha, Odell
Novartis Seeds Inc., Minneapolis, MN (812-593-7333)
S19-90. S24-92, S30-06
Ohio Ag. Res. Development Str., Wooster, OH
Century84, Charleston, Resnik
Ottilie RO Seed, Marshalltown, IA (515-753-5561)
8200, 8206, 8222, 8250, 8262, 8272, 8299, 8320, 8333, 8350, 375
Patriot Seed Co., Bowen, IL (217-842-5612)
188, 192, 196, 208, 210N, 233, 238, 251, 258, 280, 288, 298, 303, 308, 321, 330
Pioneer Hi-Bred Intl., Des Moines, IA (515-253-9570)
9172, 9204, 9233, 9245, 9254, 9281, 92852, 92891, 9304, 9306, 9321, 9342, 9343, 9352, 93A1, 9350, 93B41, 93882
Prairie Brand Seed Co., Story City, IA (800-544-8751)
PB-192, PB-194, PB-197, PB-201, PB-202, PB-210, PB-2120, PB-212E, PB-216X, PB-218X, PB-220X, PB-227, PB-235X, PB-236, PB-237X, PB-242X, PB-246, PB-255X, PB-257X, PB-264E, PB-265X, PB-266+, PB-271x, PB-2720, PB-276, PB-288, PB-293, PB-296, PB-303, PB-322, PB-326X, PB-330, PB-335, PB-337, PB-339X, PB-345, PB-346, PB-353, PB-358, PB-363, PB-382, PB-384, PB-SP19C, PB-SP20M, PB-SP21, PB-SP22M, PB-SP23, PB-SP26, PB-SP27, PB-SP28, PB-Sp29, PB-SP34, PB-SP36, PB-SP38
Producers Hybrids, Battle Creek, NE (402-675-2975)
2151, 2451, 3051, 3251, 3651, Ex6127
Profiseed Inc., Hampton, IA (515-456-4791)
1997, 2000, 2000+, 2035, 212, 2413, 2556, 2605, 2705, 2898, X197, X240
Ramy Int. Ltd., Mankato, MN (800-658-7269)
1995, 2097, 2195, 2220, 2395, 2420, 2450, 2550, 2555, 2650, 2800
Renk Seed Co., Sun Prairie, WI (608-837-7351)

TABLE 33-continued

RS1898, RS1990, RS2334, RS2595, RS2797
Renze Hybrids Inc., Carroll, IA (712-559-3301)
R1996, R1998, R2098, R2297, R2397, R2496, R2597, R2698, R2797, R2796, R2996, R3097,
R3297, R3596, R3698
Rolling Meadows Inc., Charter Oak, IA (712-678-3581)
RM9628, RM9722, RM9727, RM9730
Sand Seed Service Inc., Mercus, IA (712-376-4135)
*EXP2001, EXP2501, *EXP3530 *EXP9623, EXP9626, EXP9631A, EXP9633, *EXP9722,
*EXP9727, EXP9728, *EXP39730 *EXP9734, EXPC301, EXPS1816, SOI169, SOI260.
SOI275, SOI277, SOI353, SOI371, SOI386
Stine Seed Co., Adel, IA (515-677-2505)
1970, 1980, *2180, 2250, *2480, *2488, 2500, 2621, 2671, *2680, 2686, *2788, 2870, 3100,
3171, *3290, 3380, 3400, *3581, 3660, *3683, 3870, 3883
Terra Int. Inc., Sioux City, IA (712-233-3609)
E147, E250, E267, E277, E317, E364T, E387, TS174, TS194, TS200, TS203, TS247STS,
TS253, TS265, TS315, TS364, TS415
Thompson Agronomics, Leland, IA (515-567-3350)
EX5125, EX5315, EX5423, EX5704, EX5308, EX6245, EX6714, EX7117, EX7237, EX7418,
EX7537, EX7707, EX7730, T-3229, EX5416, EX5705, EX8754, EX7733, EX7735, EX7779, T-
3193, T-3212, T-3217, T-3222, T-3227, T-3251, T-3264, T-3310
Treley Inc., Livingston, WI (505-543-6363)
156 Brand, 196 Brand, 226 Brand, 246 Brand
UAP Seed Co., Independence, IA (319-334-6898)
3188, 3195A, *3202, 3233, 3256, 3262, 3304, 3315, *3331N, *3367A, 3368
Wilson Seeds Inc., Harlan, IA (712-755-3841)
2136, 2563, 2780, 3110, 3380

Although only exemplary embodiments of the invention have been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A method of controlling cyst nematode population in soybeans, comprising the steps of:
    planting in one growing season a first blended composition of soybean varieties, wherein said first blended composition comprises a quantity of a first cyst nematode race resistant soybean variety having resistance to a first race spectrum and a quantity of a second soybean variety selected from the group consisting of a cyst nematode race resistant soybean variety having resistance to a second race spectrum and a cyst nematode susceptible soybean variety;
    harvesting said first blended composition of soybean varieties to yield a soybean crop;
    planting in another growing season a second blended composition of soybean varieties, wherein said second blended composition comprises a quantity of a first cyst nematode race resistant soybean variety having resistance to a first race spectrum and a quantity of a second soybean variety selected from the group consisting of a cyst nematode race resistant soybean variety having resistance to a second race spectrum and a cyst nematode susceptible soybean variety;
    harvesting said second blended composition of soybean varieties to yield a soybean crop;
    rotating the growing of a first blended composition of resistant or resistant and susceptible varieties with the growing of a second blended composition of resistant or resistant and susceptible varieties over at least two growing seasons to control soybean cyst nematode population in soybean, wherein the first blended composition and the second blended composition are different.

2. The method of claim 1, wherein the first soybean variety in either the first blended composition or the second blended composition is present in the blended composition in a range of about 10% to about 90%.

3. The method of claim 2, wherein the second soybean variety in either the first blended composition or the second blended composition is present in the blended composition in a range of about 90% to about 10%.

4. The method of claim 1, wherein a quantity of a third cyst nematode race resistant soybean variety having resistance to a third race spectrum is present in the first blended composition, the second blended composition or both blended compositions.

5. The method of claim 4, wherein a blended composition of resistant and susceptible soybean varieties is grown for at least two consecutive growing seasons followed by growing a blended composition consisting of two or more resistant soybean varieties.

6. The method of claim 4, wherein a blended composition of resistant soybean varieties is grown for at least two consecutive growing seasons followed by growing a blended composition consisting of resistant and susceptible varieties.

7. The method of claim 1, wherein said rotating includes growing at least one alternate crop.

8. The method of claim 7, wherein said alternate crop is selected from the group consisting of corn, alfalfa, oats, clover, sorghum, cotton, canola, forage grasses, sunflowers, rice, a non-blended susceptible soybean variety and a non-blended resistant soybean variety.

* * * * *